US007049302B1

(12) United States Patent
Kensil

(10) Patent No.: US 7,049,302 B1
(45) Date of Patent: May 23, 2006

(54) COMPOSITIONS OF CPG AND SAPONIN ADJUVANTS AND USES THEREOF

(75) Inventor: Charlotte A. Kensil, Milford, MA (US)

(73) Assignee: Antigenics Inc., Lexington, MA (US)

( * ) Notice: Subject to any disclaimer, the term of this patent is extended or adjusted under 35 U.S.C. 154(b) by 0 days.

(21) Appl. No.: 09/369,941

(22) Filed: Aug. 6, 1999

Related U.S. Application Data

(60) Provisional application No. 60/128,608, filed on Apr. 8, 1999, provisional application No. 60/095,913, filed on Aug. 10, 1998.

(51) Int. Cl.
*A61K 48/00* (2006.01)
*A61K 45/00* (2006.01)
*A61K 39/00* (2006.01)

(52) U.S. Cl. .................... 514/44; 424/184.1; 424/278.1
(58) Field of Classification Search .................. 514/44, 514/25; 424/278.1, 184.1; 536/23.1; 435/320.1
See application file for complete search history.

(56) References Cited

U.S. PATENT DOCUMENTS

| | | | |
|---|---|---|---|
| 4,469,863 A | 9/1984 | Ts'o et al. | |
| 4,522,811 A | 6/1985 | Eppstein et al. | |
| 5,023,243 A | 6/1991 | Tullis | |
| 5,057,540 A | 10/1991 | Kensil et al. | |
| 5,273,965 A | 12/1993 | Kensil et al. | |
| 5,352,449 A | 10/1994 | Beltz et al. | |
| 5,443,829 A | 8/1995 | Kensil et al. | |
| 5,583,112 A | 12/1996 | Kensil et al. | |
| 5,650,398 A | 7/1997 | Kensil et al. | |
| 5,808,024 A * | 9/1998 | Sasaki et al. | ............... 536/23.1 |
| 5,968,909 A * | 10/1999 | Agrawal et al. | ............... 514/44 |
| 5,977,081 A | 11/1999 | Marciani | |
| 6,013,258 A * | 1/2000 | Urban et al. | ............. 424/186.1 |
| 6,231,859 B1 | 5/2001 | Kensil | |
| 6,406,705 B1 | 6/2002 | Davis et al. | ............. 424/278.1 |
| 6,524,584 B1 | 2/2003 | Kensil | |
| 6,544,518 B1 | 4/2003 | Gerard et al. | |
| 6,558,670 B1 | 5/2003 | Friede et al. | |
| 6,645,495 B1 | 11/2003 | Kensil et al. | |
| 2002/0164341 A1 | 11/2002 | Davis et al. | |
| 2003/0091599 A1 | 5/2003 | Davis et al. | |
| 2003/0161834 A1 | 8/2003 | Friede et al. | |
| 2003/0224010 A1 | 12/2003 | Davis et al. | |

FOREIGN PATENT DOCUMENTS

| | | |
|---|---|---|
| BE | 9908885 | 4/1999 |
| EP | 1005368 | 3/1998 |
| WO | WO 95/26204 | 10/1995 |
| WO | WO 98/18810 | 5/1998 |
| WO | WO 98/37919 | 9/1998 |
| WO | WO 98/40100 | 9/1998 |
| WO | WO 98/55495 | 12/1998 |
| WO | WO 99/58118 | 11/1999 |
| WO | WO 99/61056 | 12/1999 |
| WO | WO 99/62923 | 12/1999 |
| WO | WO 00/21556 | 4/2000 |
| WO | WO 00/62800 | 10/2000 |
| WO | WO 02/32450 | 4/2002 |

OTHER PUBLICATIONS

Kensil (AIDS Research Rev., 1993, vol. 3, Koff, ed., New York, NY, p. 379-390.*
Kensil (J. Immunol., Jan. 15, 1991, vol. 146, No. 2, p. 431-437.*
Definition of "explicit" by Merriam-Webster Online.*
Definition of "chemical modification" by Stedman's Medical dictionary.*
Chu et al., CpG oligodeoxynucleotides act as ajuvants that switch on T helper 1 (Th1) immunity, 1997, J. EXP. MED., vol. 186, No. 10, pp. 1623-1631.*
Weiner et al., Immunostimulatory oligodeoxynucleotides containing the CpG motif are effective as immune adjuvants in tumor antigen immunization, Spt. 1997,Proc. Natl. Acad. Sci., vol. 94 pp. 10833-10837.*
U.S. Appl. No. 09/760,506, filed Jan. 12, 2001, Kensil et al.
Agrawal et a;., 1988, Oligodeoxynucleoside phosphoramidates and phosphorothioates as inhibitors of human immunodeficiency virus. Proc Natl Acad Sci U.S.A. 85(19):7079-7083.
Agrawal S. 1992, Antisense oligonucleotides as antiviral agents. Trends Biotechnol. 10(5):152-158.
Beaucage et al., 1981, Deoxynucleotide phosphoramidites—A new class of key intermediates for deoxypolynucleotide synthesis. Tet. Let. 22:1859-1862.
Boggs et al., 1997, Characterization and modulation of immune stimulation by modified oligonucleotides. Antisense Nucleic Acid Drug Dev. 7(5):461-471.
Campbell & Peerbaye, 1992, Saponin. *Res. Immuno.* 143:526-530.
Carson et al., 1997, Oligonucleotide adjuvants for T helper 1 (Th1)-specific vaccination. J Exp Med. 186(10):1621-1622.
Chavali & Campbell, 1987, Immunomodulatory Effects of Orally-Administered Saponins and Nonspecific Resistance Against Rabies Infection. *Int. Archs. Allergy Appl. Immun.* 84:129-134.
Chavali et al., 1988, Immunopotentiation by Orally-Administered *Quillaja* Saponins : Effects in Mice Vaccinated Intraperitoneally Against Rabies. *Clin. Exp. Immunol.* 74:339-343.

(Continued)

Primary Examiner—Michael Wilson
(74) Attorney, Agent, or Firm—Jones Day

(57) ABSTRACT

Vaccine compositions of immunostimulatory oligonucleotides and saponin adjuvants and antigens and the use thereof for stimulating immunity, enhancing cell-mediated immunity, and enhancing antibody production are disclosed. Also described are immune adjuvant compositions comprising immunostimulatory oligonucleotides and saponin adjuvants, as well as methods for increasing an immune response using the same.

60 Claims, 9 Drawing Sheets

OTHER PUBLICATIONS

Chavali et al., 1987, An In Vitro Study of Immunomodulatory Effects of Some Saponins. Int. J. Immunopharmac. 9(6):675-683.

Dalsgaard, K. 1978, A study of the isolation and characterization of the saponin q1uil a . Acta Veterinia Scandinavica 69:1-40.

Elkins et al., 1999, Bacterial DNA containing CpG motiffs stimulates lymphocyte-dependent protection of mice against lethal infection with intracellular bacteria. J Immunol. 162(4):2291-2298.

Froehler B, 1986, Deoxynulceoside H-phosphate diester intermediates. Nucleic Acids Res. 14(13):5399-5407.

Froehler et al., 1986, Synthesis of DNA via deoxynucleoside H-phosphonate method. Tet. Let. 29:2619-2622.

Gaffney et al., 1988, Large-scale oligonucleotides synthesis by the H-Phosphonate method. Tet. Let. 29:2619-2622.

Garegg et al., 1986, Nucleoside H-phosphonates III. Chemical synthesis of oligodeoxyribonucleotides by the hydrogenphosphonate approach. Tet. Let. 27:4051-4054.

Garegg et al., 1986, Nucleoside H-phosphonates IV. Automated solid phase synthesis of oligoribonucleotides by the hydrogenphosphonate approach. Tet. Let. 27:4055-4058.

Goodchild, J. 1990, Conjugates of oligonucleotides: a review of their synthesis and properties. Bioconjugate Chem. 1:165.

Higuchi et al. Structure of desacylsaponins obtained fron the bark of Quillaja saponaria. Phytochemistry 26:229-235.

Kensil et al., 1992, Structure/Function relationships in adjuvants from Quillaja saponaria Molina. Vaccine 92 (Cold Spring Harbor Laboratory Press) pp. 35-40.

Kim et al., 2001, Effect of immunological adjuvant combinations on the antibody and T-cell response to vaccination with MUCI-KLH and GD3-KLH conjugates. Vaccine. 19(4-5):530-537.

Kirby et al., Effects of anticholinesterase drugs tacrine and E2020, the 5-HT3 antagonists ondansetron, and the H3 antagonist thioperamide, in models of cognition and cholinergic function. Behav Pharmacol. 1996 Nov:7(6):513-525.

Klinman et al., 1996, CpG motifs present in bacteria DNA rapidly induce lymphocytes to secrete interleukin 6, interleukin 12, and interferon gamma. Proc Natl Acad Sci U S A. 93(7):2879-2883.

Kreig et al., 1996, Oligodeoxynucleotide modifications determine the magnitude of B cell stimulation by CpG motifs. Antisense Nucleic Acid Drug Dev. 6(2):133-139.

Krieg et al., 1998, CpG DNA induces sustained IL-12 expression in vivo and resistance to Listeria monocytogenes challenge. J Immunol. 161(5):2428-2434.

Lipkin, 1995, "Vegemania: Scientists Tout the Heath Benefits of Saponins", Science News 148:392-393.

Maharaj et al., 1986, Immune Response of Mice to Inactivated Rabies Vaccine Administered Orally: Potentiation by QuillajaSaponin. Can. J. Microbiol. 32:414-420.

Marciani et al., 1991, Genetically-engineered subunit vaccine against feline leukemia virus: protective immune response in cats. Vaccine. 9(2):89-96.

Newman et al., 1992, Saponin adjuvant induction of ovalbumin-specific CD8+ cytotoxic T lymphocyte response. J Immunol. 148(8):2357-2362.

Rao & Sung, 1995, Saponins as Anticarcinogens. J. Nutr. 125:717S-725S.

Uhlmann et al., Antisense oligonucleotides: A new therapeutic principle. Chem. Rev. 9:544-584.

Hemmi et al., 2000, "A Toll-like receptor recognizes bacterial DNA," Nature 408:740-5.

Liu et al., 2002, "QS-22 structure/function studies: effect of acylation on adjuvant activity," Vaccine 20:2808-15.

Soltysik et al., 1995, "Structure/function studies of QS-21 adjuvant: assessment of triterpene aldehyde and glucuronic acid roles in adjuvant function1" Vaccine 13:1404-10.

Wagner, 2001, "Toll meets bacterial CpG-DNA," Immunity 14:499-502.

Bomford et al., 1992, "Adjuvanticity and ISCOM formation by structurally diverse saponins", Vaccine 10:572-577.

Charlotte Read Kensil, et al, 1993 "Novel Adjuvants from Quillaja Saponaria Molina", Aids Research Review, vol. 3: 279-389.

Charlotte Read Kensil, et al, 1991"Separation and Characterization of Saponins with Adjuvant Activity from Quillaja saponaria Molina Cortex", Journal of Imm., vol. 146, 431-437, No. 2.

Klinman D.M. "Therapeutic applications of CpG—containing oligodeoxynucleotides", Antisense and Nucleic Acid Drug Development, (1998 APR) 8 (2) 181-4, XP002128519, the whole document.

Kreig A.M. et al: "The role of CpG dinucleotides in DNA vaccines, " Trends in Microbiology, (1998 Jan.) 6(1) 23-7. Ref: 39, XP000857633, the whole document.

So, H.S. et al: "Effect of a novel saponin adjuvant derived from Quillaja saponaria on the immune response to recombinant hepatitis B surface antigen," Molecules and Cells, (Apr. 30, 1997).

Kensil C.R. : "Saponins as vaccine adjuvants," Critical Reviews in Therapeutic Drug Carrier Systems, (1996) 13 (1-2) 1-55. Ref: 178, XP002128521, pp. 1-2; 6-9; 22-27;and 44.

* cited by examiner

Figure 1: CTL Induced by QS-21 and CpG/QS-21

Figure 2: CTL Induced by QS-21 and CpG/QS-21

Figure 3: Antigen-specific Serum IgG1 and IgG2a

COMPOSITIONS OF CPG AND SAPONIN ADJUVANTS AND USES THEREOF

RELATED APPLICATION

This application claims the benefit of U.S. Provisional Application No. 60/128,608, filed Apr. 8, 1999, and of U.S. Provisional Application No. 60/095,913, filed Aug. 10, 1998, the contents of which are both incorporated herein by reference.

FIELD OF THE INVENTION

The present invention is in the field of immune adjuvants and vaccines. The compositions of the invention stimulate immunity, enhance cell-mediated immunity, and enhance antibody production.

BACKGROUND OF THE INVENTION

Adjuvant saponins have been identified and purified from an aqueous extract of the bark of the South American tree, *Quillaja saponaria* Molina. Among the 22 saponin peaks which were separable, the more predominant purified saponins have been identified as QS-7, QS-17, QS-18, and QS-21, also known as QA-7, QA-17, QA-18, and QA-21, respectively. These saponins have been substantially purified by various methods including high pressure liquid chromatography ("HPLC"), low pressure liquid silica chromatography, and hydrophilic interactive chromatography ("HILIC"). The substantially pure saponins have been found to be useful as immune adjuvants for enhancing immune responses in individuals. (Kensil, et al., U.S. Pat. No. 5,057,540; Kensil, et al., *J. Immunol.* 148:2357 (1991); Marciani, et al., *Vaccine* 9:89 (1991).)

Recently, oligonucleotides containing the unmethylated cytosine-guanine ("CpG") dinucleotide in a particular sequence context or motif have been shown to be potent stimulators of several types of immune cells in vitro. (Weiner, et al., *Proc. Natl. Acad. Sci.* 94:10833 (1997).) An immunostimulatory oligonucleotide comprising an unmethylated CpG motif is an dinucleotide within the oligonucleotide that consistently triggers an immunostimulatory response and release of cytokines. CpG motifs can stimulate monocytes, macrophages, and dendritic cells that can produce several cytokines, including the T helper 1 ("Th 1") cytokine interleukin ("IL") 12. (Carson, et al., *J. Exp. Med.* 186:1621 (1997).) This effect causes the induction of IFN-γ secretion by natural killer cells, which in turn, activates macrophages and enhances immunoglobulin isotype switching to IgG2a, a hallmark of T helper cell immunity and differentiation. (Chu, et al., *J. Exp. Med.* 186:1623 (1997).) Klinman, et al., have shown that a DNA motif consisting of an unmethylated CpG dinucleotide flanked by two 5' purines (GpA or ApA) and two 3' pyrimidines (TpC or TpT) optimally stimulated B cells to produce IL-6 and IL-12 and stimulated CD4+ T cells to produce IL-6 and IFN-γ both in vitro and in vivo. (Klinman, et al., *Proc. Natl. Acad. Sci.*, 93:2879 (1996).) Davis, et al., the contents of which are incorporated herein by reference, discovered that nucleic acids containing at least one unmethylated CpG dinucleotide may affect the immune response of a subject (Davis, et al., WO 98/40100, PCT/US98/04703).

SUMMARY OF THE INVENTION

Since immunity plays an important role in the protective response to infection with certain microbial agents, a need exists to characterize other novel adjuvants that may safely induce immunity. Such adjuvants may be potentially incorporated in future human vaccines. Surprisingly, a combination of an oligonucleotide comprising at least one unmethylated CpG dinucleotide and a saponin adjuvant was found to be a powerful stimulator of cell-mediated immunity compared to either adjuvant alone. Antibody titers (antigen-specific) in response to vaccination were significantly higher for vaccines comprising a CpG-containing oligonucleotide/saponin adjuvant combination compared to either saponin or CpG alone and represented a positive synergistic adjuvant effect. Together, these results establish that an immune adjuvant composition comprising an immunostimulatory oligonucleotide comprising at least one unmethylated CpG dinucleotide and a saponin adjuvant is a candidate adjuvant composition for vaccines to induce immunity. Accordingly, the present invention provides novel vaccine compositions which comprise an immunostimulatory oligonucleotide, a saponin adjuvant, and an antigen. Methods for increasing the immune response to an antigen by administrating the inventive vaccine compositions and/or immune adjuvant compositions are other embodiments described herein.

DESCRIPTION OF THE PREFERRED EMBODIMENTS

Figure 1:
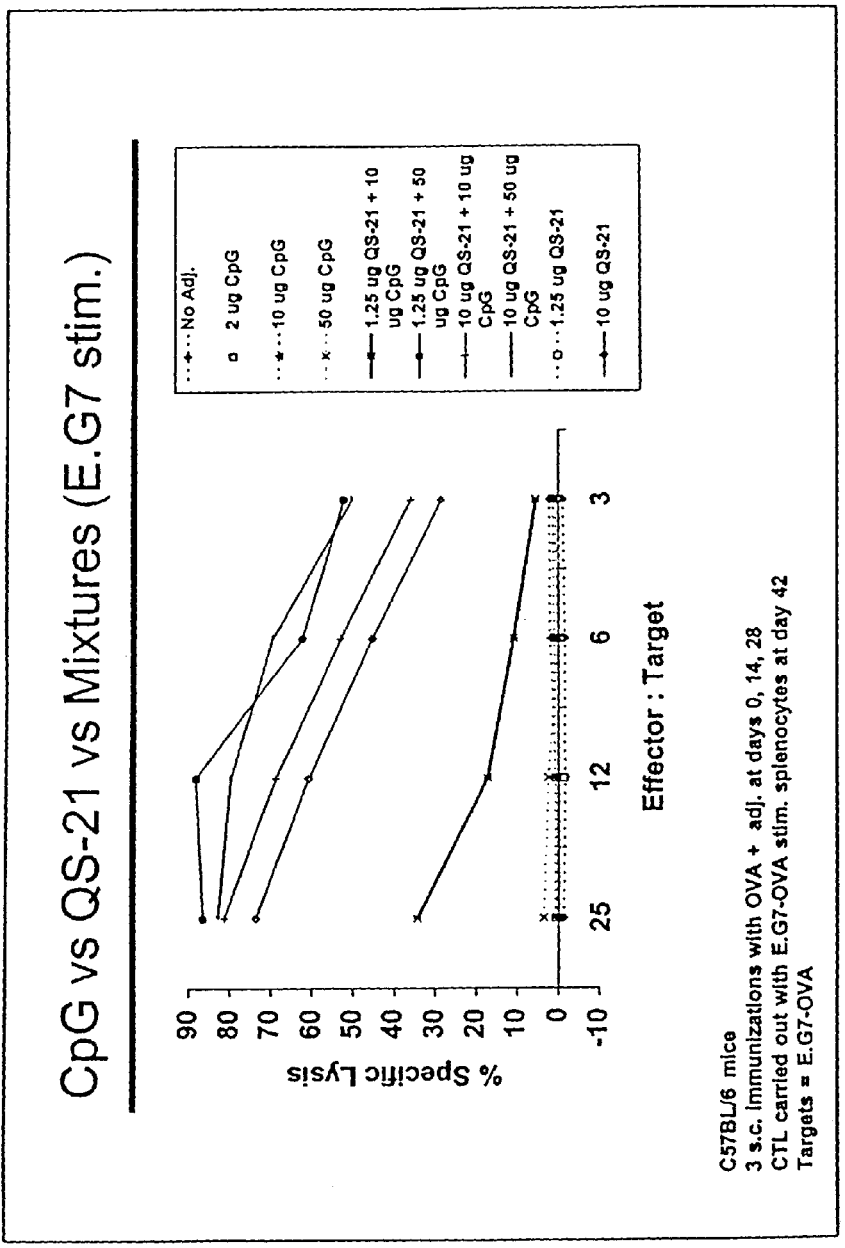
FIG. 1 depicts a graph showing the enhancement of a cell-mediated immune response by QS-21 and CpG oligonucleotide/QS-21 combination, as evidenced by the CTL induction.

The term "saponin" as used herein includes glycosidic triterpenoid compounds which produce foam in aqueous solution, have hemolytic activity in most cases, and possess immune adjuvant activity. The invention encompasses the saponin per se, as well as natural and pharmaceutically acceptable salts and pharmaceutically acceptable derivatives. The term "saponin" also encompasses biologically active fragments thereof.

The saponins of the present invention may be obtained from the tree Quillaja saponaria Molina. (Dalsgaard, Acta Veterinia Scandinavica, 69:1 (1978).) A partially purified saponin enriched extract, prepared as described by Dalsgaard, ("Quil-A") has adjuvant activity. Such an extract can be further separated. Among the 22 saponin peaks which were separable, the more predominant purified saponins have been identified as QS-7, QS-17, QS-18, and QS-21, also known as QA-7, QA-17, QA-18, and QA-21, respectively. (Kensil, et al., U.S. Pat. No. 5,057,540.) These saponins have been substantially purified by various methods including HPLC, low pressure liquid silica chromatography, and HILIC.

As described in Kensil, et al., U.S. Pat. No. 5,057,540, the contents of which are fully incorporated by reference herein, the adjuvant activity of such saponins may be determined by any of a number of methods known to those of ordinary skill in the art. The increase in antibody titer of antibody against specific antigen upon administration of an adjuvant may be used as a criteria for adjuvant activity. (Bomford, Int. Archs. Allergy Appl. Immun. 77:409 (1985).) Briefly, one such test involves injecting CD-1 mice intradermally with an antigen (for instance, i.e., bovine serum albumin, ("BSA")) mixed with varying amounts of the potential adjuvant. Sera was harvested from the mice two weeks later and tested by ELISA for anti-BSA antibody.

Another such test involves injecting inbred mice such as C57BL/6 or Balb/c by subcutaneous route with a protein antigen such as ovalbumin ("OVA") or a polysaccharide antigen such as pneumococcal polysaccharide, mixed with the potential adjuvant. Sera harvested form the mice after one, tow, or three immunizations could be harvested and tested by ELISA for antigen-specific antibody (total immunoglobulin) or for specific mouse IgG subclassses such as IgG1 or IgG2a. Another such test involves injecting C57BL/6 mice with OVA, harvesting spleens after one, two, or three immunizations, stimulating splenocytes with antigen, and then assaying for cytolytic T lymphocyte activity ("killing") of OVA-peptide-expressing target cells. Alternative, a proliferative response could be measured in an in vitro assay by measuring the uptake of $^3$H-thymidine by antigen-stimulated splenocytes obtained from immunized animals.

"QS-21" designates the mixture of components QS-21-V1 and QS-21-V2 which appear as a single peak on reverse phase HPLC on Vydac C4 (5 μm particle size, 300 Å pore, 4.6 mm ID×25 cm length) in 40 mM acetic acid in methanol/water (58/42, v/v). The component fractions are referred to specifically as QS-21-V1 and QS-21-V2 when describing experiments performed on the further purified components.

According to Kensil, et al., U.S. Pat. No. 5,583,112, the contents of which are fully incorporated by reference herein, the carboxyl group on the glucuronic acid of Quillaja saponaria Molina can be conjugated to a protein, a peptide, or a small molecule containing a primary amine. Thus, the present invention relates to a chemically modified saponin adjuvant or a fraction thereof obtainable from a crude Quillaja saponaria Molina extract, wherein the chemically modified saponin or fraction thereof comprises at least one of QS-17, QS-18, QS-21, QS-21-V1, and QS-21-V2, and wherein the modified saponin retains adjuvant activity.

The term "partially pure" means saponins partially separated from compounds normally associated with the saponin in its natural state.

The term "substantially pure" means substantially free from compounds normally associated with the saponin in its natural state and exhibiting constant and reproducible chromatographic response, elution profiles, and biologic activity. The term "substantially pure" is not meant to exclude artificial or synthetic mixtures of the saponin with other compounds.

The present invention may also employ immunostimulatory saponins isolated from other plant species. For example, a saponin from Dolichos lablab has been shown to be useful as an adjuvant (Katayan, et al., Vaccine 17:2733 (1999)).

The term "immunostimulatory oligonucleotide comprising at least one unmethylated CpG dinucleotide" means an oligonucleotide that has been shown to activate the immune system. The immunostimulatory oligonucleotide may, preferably, comprise at least one unmethylated CpG dinucleotide. A "CpG motif" is a stretch of DNA comprising one or more CpG dinucleotides within a specified sequence. The oligonucleotide comprising the CpG motif may be as short as 4–40 base pairs in length. The immunostimulatory oligonucleotide containing the CpG motif may be a monomer or part of a multimer. Alternatively, the CpG motif may be a part of the sequence of a vector that also presents a DNA vaccine. It may be single-stranded or double-stranded. It may be prepared synthetically or produced in large scale in plasmids. One embodiment of the invention covers the immunostimulatory oligonucleotide which contains a CpG motif having the formula 5'$X_1$CG$X_2$3', wherein at least one nucleotide separates consecutive CpGs, and wherein $X_1$ is adenine, guanine, or thymine and $X_2$ is cytosine, thymine or adenine. In a preferred embodiment, the CpG motif comprises TCTCCCAGCGTGCGCCAT (SEQ ID NO:1; also known as "1758") or TCCATGACGTTCCTGACGTT (SEQ ID NO:2; also known as "1826").

DNA containing unmethylated CpG dinucleotide motifs in the context of certain flanking sequences has been found to be a potent stimulator of several types of immune cells in vitro. (Ballas, et al., J. Immunol. 157:1840 (1996); Cowdrey, et al., J. Immunol. 156:4570 (1996); Krieg, et al., Nature 374:546 (1995).) Depending on the flanking sequences, certain CpG motifs may be more immunostimulatory for B cell or T cell responses, and preferentially stimulate certain species. When a humoral response is desired, preferred immunostimulatory oligonucleotides comprising an unmethylated CpG motif will be those that preferentially stimulate a B cell response. When cell-mediated immunity is desired, preferred immunostimulatory oligonucleotides comprising at least one unmethylated CpG dinucleotide will be those that stimulate secretion of cytokines known to facilitate a CD8+ T cell response.

The immunostimulatory oligonucleotides of the invention may be chemically modified in a number of ways in order to stabilize the oligonucleotide against endogenous endonucleases. For example, the oligonucleotides may contain other than phosphodiester linkages in which the nucleotides at the 5' end and/or 3' end of the oligonucleotide have been replaced with any number of non-traditional bases or chemical groups, such as phosphorothioate-modified nucleotides. The immunostimulatory oligonucleotide comprising at least one unmethylated CpG dinucleotide may preferably be modified with at least one such phosphorothioate-modified nucleotide. Oligonucleotides with phosphorothioate-modified linkages may be prepared using methods well known in the field such as phosphoramidite (Agrawal, et al., *Proc. Natl. Acad. Sci.* 85:7079 (1988)) or H-phosphonate (Froehler, et al., *Tetrahedron Lett.* 27:5575 (1986)). Examples of other modifying chemical groups include alkylphosphonates, phosphorodithioates, alkylphosphorothioates, phosphoramidates, 2-O-methyls, carbamates, acetamidates, carboxymethyl esters, carbonates, and phosphate triesters. Oligonucleotides with these linkages can be prepared according to known methods (Goodchild, *Chem. Rev.* 90:543 (1990); Uhlmann, et al., *Chem. Rev.* 90:534 (1990); and Agrawal, et al., *Trends Biotechnol.* 10:152 (1992)).

The term "immune adjuvant" as used herein refers to compounds which, when administered to an individual or tested in vitro, increase the immune response to an antigen in the individual or test system to which the antigen is administered. Preferably, such individuals are mammals, and more preferably, the mammals are humans, however, the invention is not intended to be so limiting. Any animal which may experience the beneficial effects of the vaccines of the invention are within the scope of animals which may be treated according to the claimed invention. Some antigens are weakly immunogenic when administered alone, i.e., inducing no or weak antibody titers or cell-mediated immune response. An immune adjuvant may enhance the immune response of the individual by increasing antibody titers and/or cell-mediated immunity. The adjuvant effect may also lower the dose of the antigen effective to achieve an immune response in the individual.

In a first aspect of the invention, an immune adjuvant composition comprising a saponin adjuvant and an immunostimulatory oligonucleotide may be administered. More preferably, such immune adjuvant composition may increase the immune response to an antigen in an individual or a test system to which the antigen is administered. Preferably, the saponin adjuvant is a saponin from *Quillaja saponaria* Molina. More preferably, the saponin adjuvant is a partially pure or substantially pure saponin from *Quillaja saponaria* Molina. Preferably, the partially pure saponin may comprise QS-7, QS-17, QS-18, and/or QS-21 and may comprise other saponins. Preferably, the substantially pure saponin adjuvant is QS-7, QS-17, QS-18, or QS-21. Most preferably, the substantially pure saponin adjuvant is QS-21. Alternatively, the immune adjuvant composition may comprise more than one substantially pure saponin adjuvant with the immunostimulatory oligonucleotide. In a further preferred embodiment, the saponin adjuvant may cover a chemically modified saponin adjuvant or a fraction thereof obtainable from a crude *Quillaja saponaria* Molina extract, wherein the chemically modified saponin or fraction thereof comprises at least one of QS-17, QS-18, QS-21, QS-21-V1, and QS-21-V2, and wherein the chemically modified saponin retains adjuvant activity. The immunostimulatory oligonucleotide, preferably, comprises at least one unmethylated CpG dinucleotide. The CpG dinucleotide is preferably a monomer or multimer. Another preferred embodiment of the CpG motif is as a part of the sequence of a vector that also presents a DNA vaccine. Yet another embodiment of the immune adjuvant composition is directed to the immunostimulatory oligonucleotide, wherein the immunostimulatory oligonucleotide is modified. The particular modification may comprise at least one phosphorothioate-modified nucleotide. Further, the immunostimulatory oligonucleotide having at least one unmethylated CpG dinucleotide may comprise a CpG motif having the formula 5'$X_1$CG$X_2$3', wherein at least one nucleotide separates consecutive CpGs, and wherein $X_1$ is adenine, guanine, or thymine, and $X_2$ is cytosine, thymine, or adenine. The CpG motif may preferentially be TCTCCCAGCGTGCGCCAT [SEQ ID NO.:1] or TCCATGACGTTCCTGACGTT [SEQ ID NO.:2]

In a second aspect, the invention is directed to a method for increasing the immune response to an antigen in an individual or a test system to which the antigen is administered comprising administering an effective amount of an immune adjuvant composition comprising a saponin adjuvant and an immunostimulatory oligonucleotide further. Preferably, the saponin adjuvant is a saponin from *Quillaja saponaria* Molina. More preferably, the saponin adjuvant is a partially pure or a substantially pure saponin from *Quillaja saponaria* Molina. The method may also embody an immune adjuvant composition comprising more than one substantially pure saponin adjuvant and immunostimulatory oligonucleotide. The substantially pure saponin adjuvant is preferably QS-7, QS-17, QS-18, or QS-21. Most preferably, the substantially pure saponin adjuvant is QS-21. In a further preferred embodiment, the saponin adjuvant may cover a chemically modified saponin adjuvant or a fraction thereof obtainable from a crude *Quillaja saponaria* Molina extract, wherein the chemically modified saponin or fraction thereof comprises at least one of QS-17, QS-18, QS-21, QS-21-V1, and QS-21-V2, and wherein the chemically modified saponin retains adjuvant activity. In a preferred embodiment of the method, the immunostimulatory oligonucleotide comprises at least one unmethylated CpG dinucleotide. The CpG motif is preferably a monomer or a multimer. Another preferred embodiment of the method includes the CpG motif as a part of the sequence of a vector that presents a DNA vaccine. Yet another embodiment is directed to the method wherein the immunostimulatory oligonucleotide comprises at least one unmethylated CpG dinucleotide, and wherein furthermore, the immunostimulatory oligonucleotide may be chemically modified to stabilize the oligonucleotide against endogenous endonucleases. The modification may comprise at least one phosphorothioate-modified nucleotide. Further, the method may be directed, in part, to the immunostimulatory oligonucleotide having at least one unmethylated CpG dinucleotide comprising a CpG motif having the formula 5'$X_1$CG$X_2$3', wherein at least one nucleotide separates consecutive CpGs, and wherein $X_1$ is adenine, guanine, or thymine, and $X_2$ is cytosine, thymine, or adenine. In another preferred method, the unmethylated CpG motif is TCTCCCATCGTGCGCCAT [SEQ ID NO.:1] or TCCATGACGTTCCTGACGTT [SEQ ID NO.:2]

The term "vaccine composition" herein refers to a composition capable of producing an immune response. A vaccine composition, according to the invention, would produce immunity against disease in individuals. The combination of saponin and immunostimulatory oligonucleotide of the present invention may be administered to an individual to enhance the immune response to any antigen. Preferably, the vaccine composition stimulates immunity. More preferably, the vaccine composition enhances antibody production to an antigen and enhances a cell-mediated immune response to an antigen.

The vaccine composition of the invention may enhance antibody production to an antigen in a positive synergistic manner. The synergistic adjuvant effect of the immunostimulatory oligonucleotide and the saponin adjuvant described herein may be shown in a number of ways. For example, a synergistic adjuvant effect may be demonstrated as an increase in the maximum expected immune response. One may expect an additive effect of combining two adjuvants. Specifically, if one adjuvant, used at optimum doses, produces "X" and the other adjuvant, also used at optimum doses, produces "Y" antibody, then the combination may be expected to produce "X+Y" if the result is additive and not synergistic. A maximum level of response that is considerably higher than "X+Y" would be considered a synergistic effect and would be unexpected. A second indication of synergism would be the appearance of a substantial adjuvant effect at doses that are normally not expected to produce an adjuvant effect. A third indication of synergism would be the appearance of an immune response with earlier kinetics than expected for either adjuvant alone.

Further, typical antigens suitable for the enhanced immune response include antigens derived from any of the following: viruses, such as influenza, feline leukemia virus, feline immunodeficiency virus, HIV-1, HIV-2, rabies, measles, hepatitis B, or hoof and mouth disease; bacteria, such as anthrax, diphtheria, Lyme disease, pneumococcus, or tuberculosis; or protozoans, such as *Babeosis bovis* or *Plasmodium*. The antigen may preferably be a protein, a peptide, a polysaccharide, a lipid, a glycolipid, a phospholipid, or a nucleic acid encoding the antigenic protein or peptide of interest. The antigens may be purified from a natural source, synthesized by means of solid phase synthesis, or may be obtained by means of genetic engineering.

Accordingly, in a third aspect, the invention also encompasses a vaccine composition comprising a saponin adjuvant, an immunostimulatory oligonucleotide, and an antigen. The saponin adjuvant may be partially pure or substantially pure saponin from *Quillaja saponaria* Molina. The vaccine compositions may also comprise more than one partially pure or substantially pure saponin adjuvant, an immunostimulatory oligonucleotide further comprising at least one unmethylated CpG motif, and an antigen. Preferably, the partially pure saponin adjuvant comprises QS-7, QS-17, QS-18, and/or QS-21 and may comprise other saponins. Preferably, the substantially pure saponin adjuvant is QS-7, QS-17, QS-18, or QS-21. A further preferred embodiment encompasses saponin adjuvants wherein a chemically modified saponin adjuvant or a fraction thereof obtainable from a crude *Quillaja saponaria* Molina extract, wherein the chemically modified saponin or fraction thereof comprises at least one of QS-17, QS-18, QS-21, QS-21-V1, and QS-21-V2, and wherein the chemically modified saponin retains adjuvant activity. Most preferably, the partially pure or substantially pure saponin adjuvant in the vaccine composition is QS-21. The immunostimulatory oligonucleotide may preferably comprise at least one unmethylated CpG dinucleotide. The CpG motif may preferably be a monomer or a multimer. Another preferred embodiment of the CpG motif is as a part of the sequence of a vector that also presents a DNA vaccine. Yet another embodiment of the vaccine composition described herein is directed to the immunostimulatory oligonucleotide comprising at least one unmethylated CpG dinucleotide comprises a chemical modification. More particularly, the immunostimulatory oligonucleotide may be modified with at least one phosphorothioate-modified nucleotide. Further, the immunostimulatory oligonucleotide having at least one unmethylated CpG dinucleotide of the vaccine composition comprises a CpG motif having the formula $5'X_1CGX_23'$, wherein at least one nucleotide separates consecutive CpGs, and wherein $X_1$ is adenine, guanine, or thymine, and $X_2$ is cytosine, thymine, or adenine. The unmethylated CpG motif according to this aspect of the invention may preferentially comprise TCTCCCAGCGTGCGCCAT [SEQ ID NO.:1] or TCCATGACGTTCCTGACGTT [SEQ ID NO.:2]

A fourth aspect of the invention encompasses a method of stimulating immunity to an antigen in an individual comprising administering an effective amount of a vaccine composition comprising an antigen, a partially pure or substantially pure saponin adjuvant, and an immunostimulatory oligonucleotide. The method also embodies a vaccine composition comprising more than one partially pure or substantially pure saponin adjuvant, an immunostimulatory oligonucleotide, and an antigen. Preferably, the partially pure saponin adjuvant comprises QS-7, QS-17, QS-18, and/or QS-21 and may comprise other saponins. Preferably, the substantially pure saponin adjuvant comprises QS-7, QS-17, QS-18, or QS-21. Most preferably, according to this method, the partially pure or substantially pure saponin adjuvant is QS-21. The saponin adjuvant may preferably be a chemically modified saponin adjuvant or a fraction thereof obtainable from a crude *Quillaja saponaria* Molina extract, wherein the chemically modified saponin or fraction thereof comprises at least one of QS-17, QS-18, QS-21, QS-21-V1, and QS-21-V2, and wherein the chemically modified saponin retains adjuvant activity. Preferably, the method comprises administering an immunostimulatory oligonucleotide which further comprises at least one unmethylated CpG dinucleotide. The CpG dinucleotide therein is a monomer or a multimer. Another preferred embodiment of the method includes the CpG motif as a part of the sequence of a vector that also presents a DNA vaccine. Yet another embodiment of the method disclosed herein is directed to the immunostimulatory oligonucleotide comprising at least one unmethylated CpG dinucleotide, wherein the immunostimulatory oligonucleotide may be chemically modified to increase its stability to endogenous endonucleases. Such a modification may comprise at least one phosphorothioate-modified nucleotide. Further, the immunostimulatory oligonucleotide having at least one unmethylated CpG dinucleotide may comprise a CpG motif having the formula $5'X_1CGX_23'$, wherein at least one nucleotide separates consecutive CpGs, and wherein $X_1$ is adenine, guanine, or thymine, and $X_2$ is cytosine, thymine, or adenine. In another preferred embodiment, the unmethylated CpG motif is TCTCCCAGCGTGCGCCAT [SEQ ID NO.:1] or TCCATGACGTTCCTGACGTT [SEQ ID NO.:2]

Other useful methods for the vaccine composition include enhancing antibody production to an antigen and enhancing cell-mediated immunity. More preferably, the vaccine composition enhances antibody production to an antigen and enhances a cell-mediated immunity. Most preferably, the vaccine composition enhances antibody production to an antigen in a positive synergistic manner.

Administration of the compositions of the present invention may be by parenteral, intravenous, intramuscular, subcutaneous, intranasal, oral, mucosal, or any other suitable means. The dosage administered may be dependent upon the age, weight, kind of concurrent treatment, if any, and nature of the antigen administered. The initial dose may be followed up with a booster dosage after a period of about four weeks to enhance the immunogenic response. Further booster dosages may also be administered. The composition may be given as a single injection of a mixed formulation of saponin, oligonucleotide, and antigen or as separate injections given at the same site within a short period of time (i.e., 0–2 days).

The effective compositions of the present invention may be employed in such forms as capsules, liquid solutions, suspensions or elixirs for oral administration, or sterile liquid forms such as solutions or suspensions. Any inert acceptable carrier may preferably be used, such as saline, or PBS, or any such acceptable carrier in which the compositions of the present invention have suitable solubility properties for use of the present invention.

EXAMPLES

A well-established animal model was used to assess whether formulations of CpG oligonucleotide and QS-21 together could function as an immune adjuvant. In brief, experiments were set up to compare QS-21 to the recently reported adjuvant CpG motif. A CpG sequence (e.g., 1758), reported to serve as an adjuvant for a B-cell lymphoma idiotype-KLH vaccine in mice, was selected. One experiment evaluated whether the CpG motif, alone or in combination with QS-21, can serve as an adjuvant for a subunit vaccine, e.g., OVA, in mice in inducing CTL responses. This work included a dose range experiment with CpG to determine the optimum dose.

In addition to comparing CpG and QS-21 as adjuvants, a second experiment combining CpG oligonucleotide with suboptimal doses of QS-21 (e.g., 1.25 µg) was conducted to assess whether CpG oligonucleotide can affect the adjuvant effect of QS-21.

Also, an experiment was performed to determine whether the CpG and QS-21 combination could enhance antibody production, specifically the isotype profile of a antigen-specific antibody response.

Finally, a series of experiments were performed to determine whether a combination of CpG oligonucleotide and saponin would enhance antibody production in a positive synergistic manner. This work used vaccine formulations of pneumococcal Type 14 polysaccharide and QS-21 and CpG oligonucleotide and evaluated specific antibody titers harvested from mice on days 21 and 42 after immunization on days 0 and 28. Another CPG sequence (e.g., 1826), reported to serve as an adjuvant for hen egg lysozyme in mice, was selected.

The experiments were done using materials from the following suppliers: OVA, Grade VI (Sigma); pneumococcal Type 14 polysaccharide (ATCC); QS-21 (Aquila); CpG oligonucleotides included the phosphorothiate-modified sequence 1758 TCTCCCAGCGTGCGCCAT [SEQ ID NO.:1] and phosphorothiate-modified sequence 1826 TCCATGACGTTCCTGACGTT [SEQ ID NO.:2] (Life Technologies (Gibco)).

Example 1

CTL Induced by OS-21 and CpG/OS-21

C57BL/6 mice (5 per group, female, 8–10 weeks of age) were immunized by subcutaneous route at days 1, 15, and 29. The vaccines were 25 µg OVA antigen plus the indicated doses of adjuvant in a total volume of 0.2 ml phosphate-buffered saline. The CpG motif used in this experiment was a phosphorothioate-modified oligonucleotide 1758 with a sequence of TCTCCCAGCGTGCGCCAT [SEQ ID NO.:1] (Weiner, et al., *Proc. Natl. Acad. Sci.* 94:10833 (1997).) Splenocytes were removed at day 42 for use as effector cells in the CTL assay. They were stimulated in vitro for 6 days with mitomycin C-treated E.G7-OVA cells and then used in a standard $^{51}$Cr release CTL assay. E.G7-OVA cells (loaded with $^{51}$Cr) were used as target cells. The background lysis of EL4 cells (not transfected by OVA) was subtracted from the lysis of E.G7-OVA cells to obtain a percent (%) antigen-specific lysis.

The results, as shown in FIG. 1, indicate that no lysis was observed in the absence of adjuvant, with any CpG dose, or with 1.25 µg of QS-21 (suboptimal dose). However, the suboptimal dose of QS-21, in combination with CpG, induced significant CTL. The results show a substantial adjuvant effect at doses that are normally not expected to produce such an adjuvant effect. This positive synergistic effect was most notable at the higher dose of CpG (50 µg). The adjuvant effect was comparable to that achieved with the optimal 10 µg QS-21 control.

Example 2

CTL Induced by OS-21 and CpG/OS-21

Splenocytes from mice immunized as described in FIG. 1 were used in a CTL assay. Splenocytes were stimulated in vitro with denatured OVA for six days prior to use in the CTL assay. The assay was carried out against E.G7-OVA cells as described in Example 1.

Figure 2:
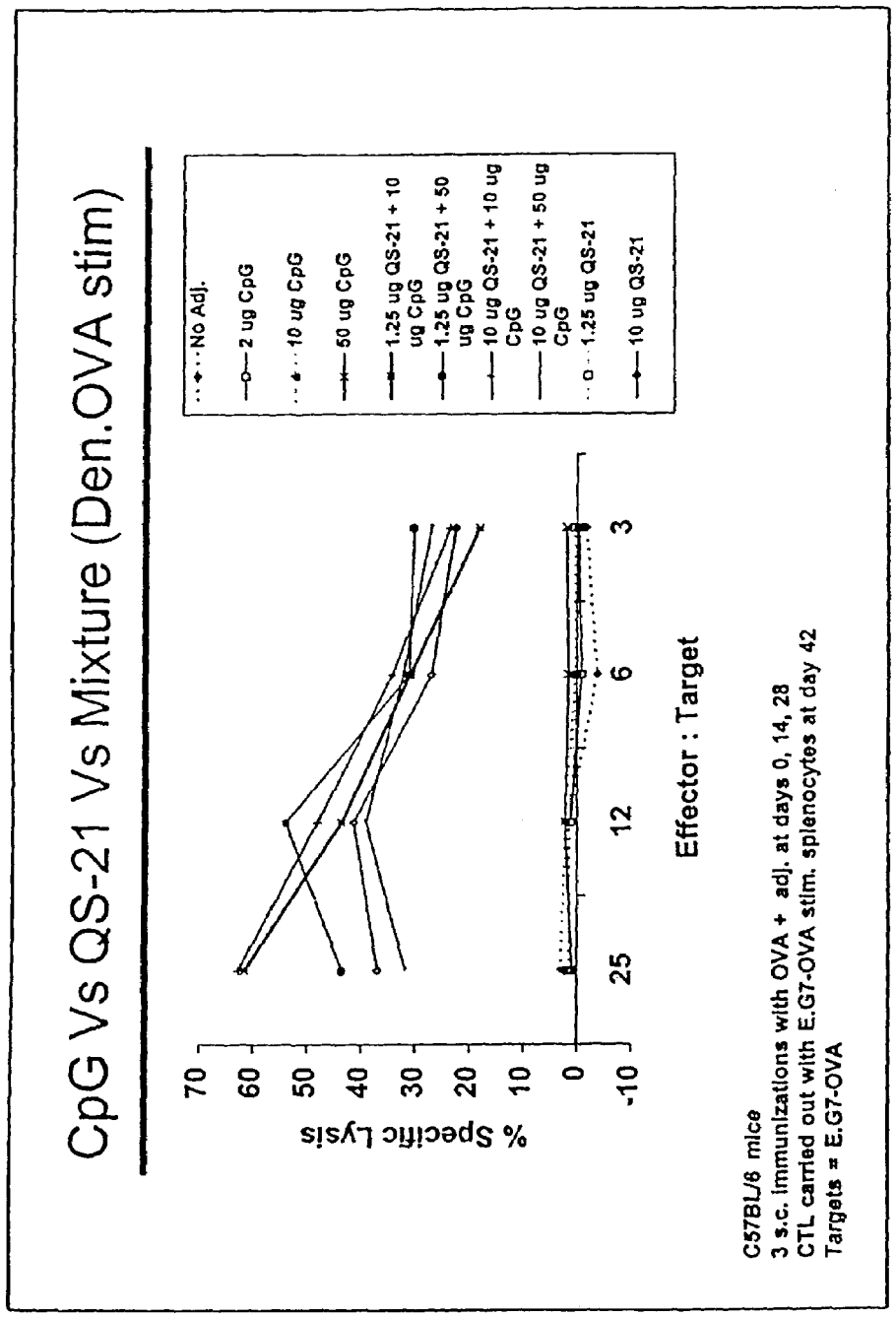
FIG. 2 provides a graph showing the enhancement of a cell-mediated immune response by QS-21 and CpG oligonucleotide/QS-21 combination, as evidenced by the CTL induction.

As evident from the results in FIG. 2, no lysis was observed in the absence of adjuvant, with any CpG dose, or with 1.25 µg of QS-21 (suboptimal dose). However, the suboptimal dose of QS-21, in combination with CpG, induced significant CTL (comparable to the optimal 10 µg QS-21 control). The results illustrate the positive synergism between the CpG and the QS-21 that was unexpected at a suboptimal dose.

Example 3

Antigen-specific Serum IgG1 and IgG2a

Figure 3:
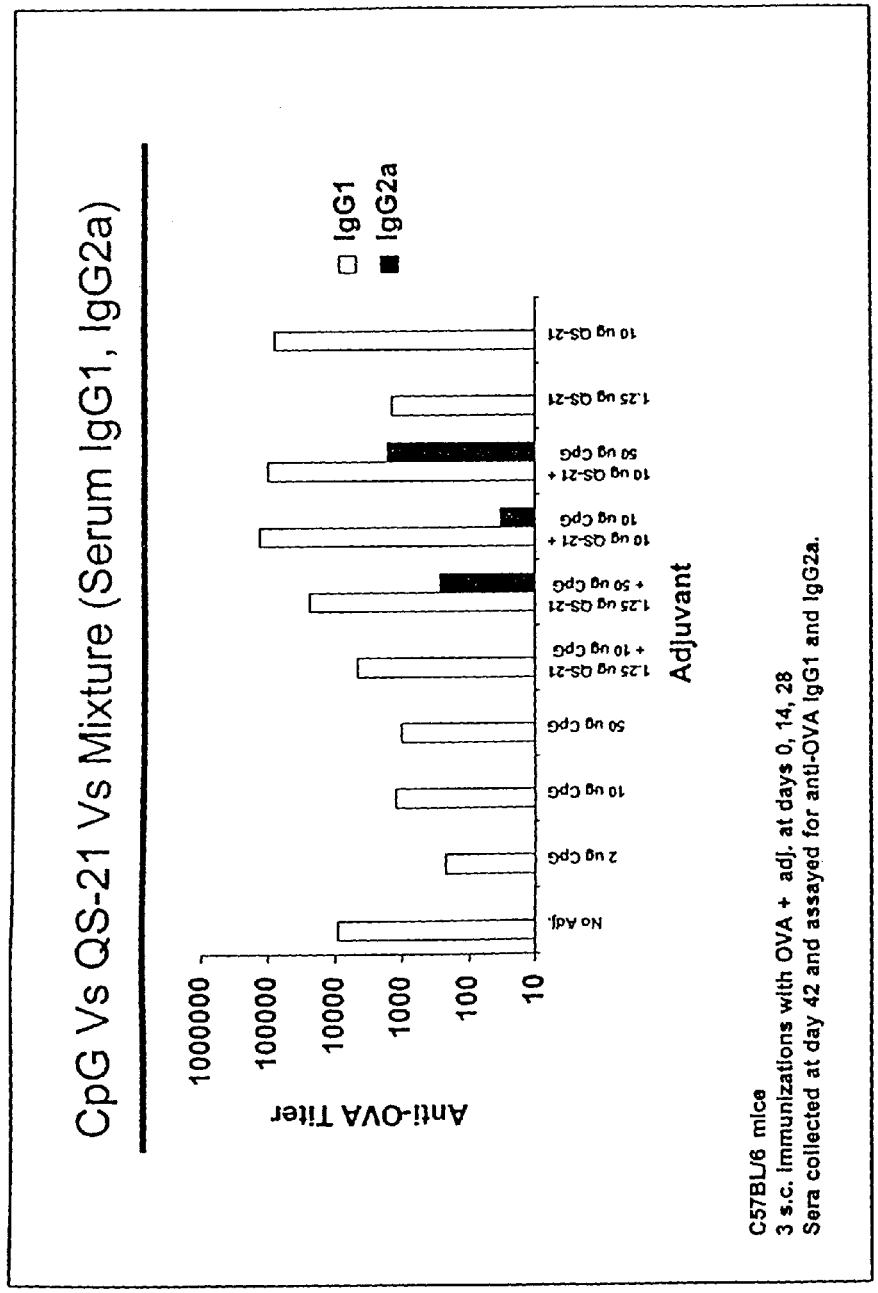
FIG. 3 shows a bar graph of enhanced antibody production, particularly the antibody subclasses such as IgG2a that are influenced by Th 1 cytokines.

Serum titers to OVA were determined by EIA on sera collected on day 42 from the mice immunized as described in Example 1. IgG subclass IgG1 and IgG2a titers were determined for individual mice (5 mice per group) and are plotted as a geometric mean titer. The IgG1 titers were highest in groups receiving QS-21 alone (at the 10 µg dose) or 10 µg QS-21 in combination with either 10 or 50 µg (approximate 10 fold enhancement over the unadjuvanted group) as seen in FIG. 3. The IgG2a response was not detectable in any groups except for the combination of 10 µg QS-21 (optimal dose) with 10 or 50 µg CpG and the combination of 1.25 µg QS- 21 (suboptimal dose) with 50 µg CpG. IgG2a was not detected with any CpG dose used alone, with any QS-21 dose used alone, or in the unadjuvanted group.

Example 4

Antibody Induced by OS-21 and OS-21/CpG to Pneumococcal Polysaccharide Antigen

BALB/c mice (5 mice per group, female, 8–10 weeks of age) were immunized by subcutaneous route at day 0 only or at days 0 and 28. The vaccines were 0.5 µg pneumococcal Type 14 polysaccharide plus the indicated doses of adjuvant in a total volume of 0.2 ml phosphate-buffered saline. The immunostimulatory motif CpG used in this experiment was a phosphorothioate-modified oligonucleotide 1826 with a sequence of TCCATGACGTTCCTGACGTT [SEQ ID NO.:2] (Chu, et al., *Exp. Med.* 186:1623–1631 (1997)). QS-21 was used at a dose of 1.25 μg or 10 μg. CpG ODN 1826 was used at a dose of only 10 μg.

Figure 4:
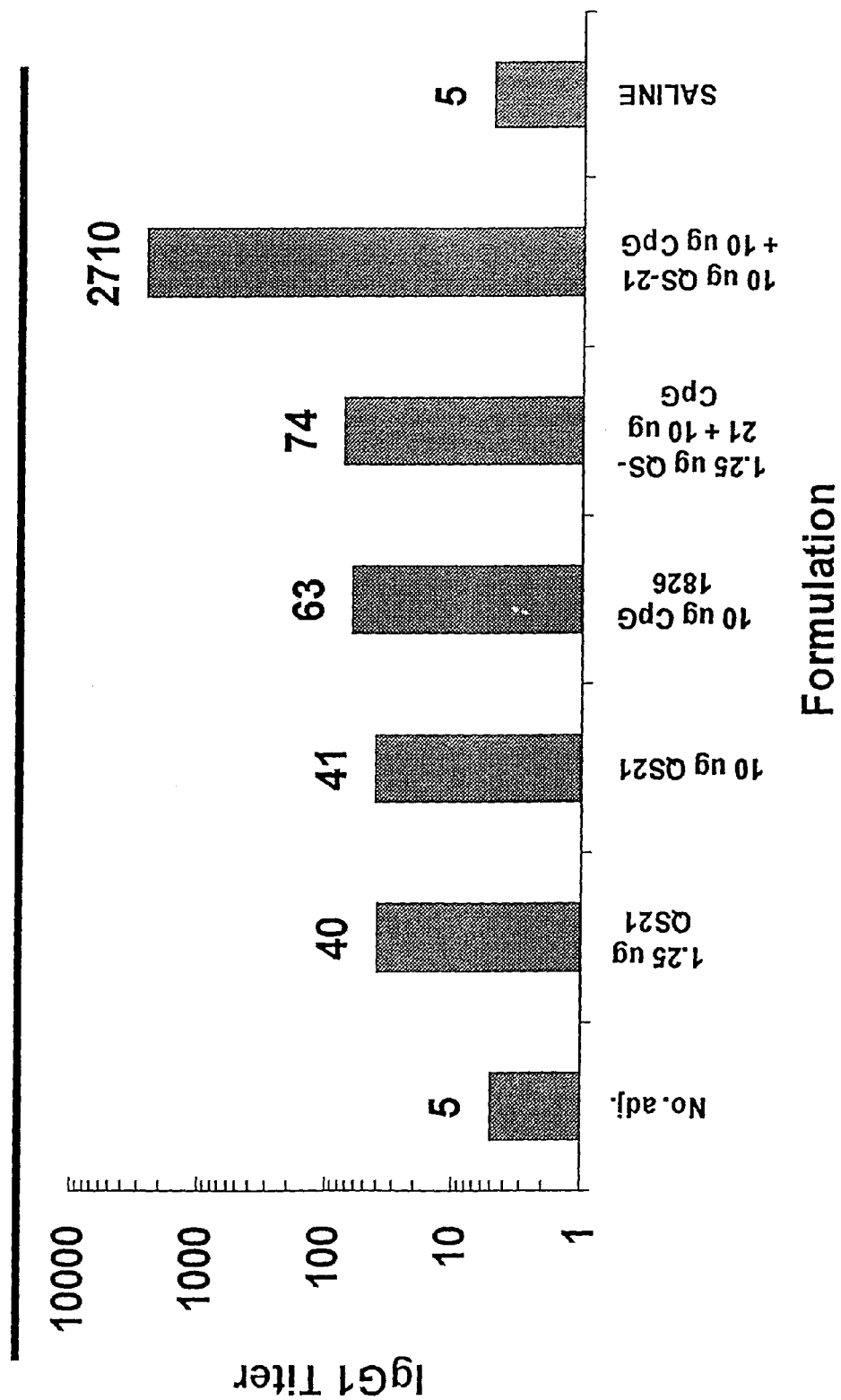
FIG. 4 shows a bar graph of IgG1 titers specific for pneumococcal Type 14 polysaccharide with the various formulations and for combinations of QS-21 and CpG oligonucleotide in mouse sera collected 21 days after a first immunization given on day 0.
Figure 5:
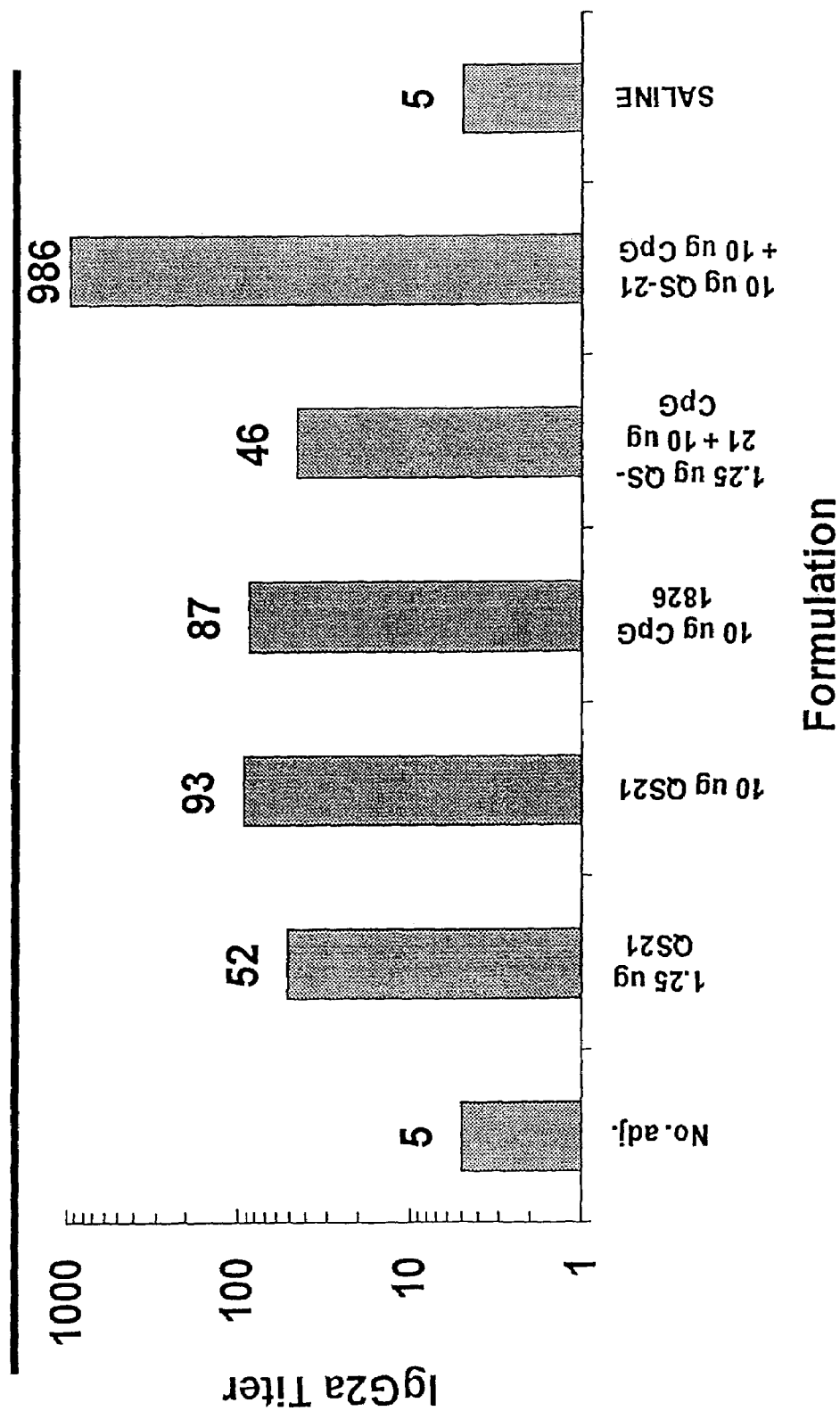
FIG. 5 illustrates a bar graph of IgG2a titers specific for pneumococcal Type 14 polysaccharide with the various formulations and/or combinations of QS-21 and CpG oligonucleotide in mouse sera collected 21 days after a first immunization given on day 0.
Figure 6:
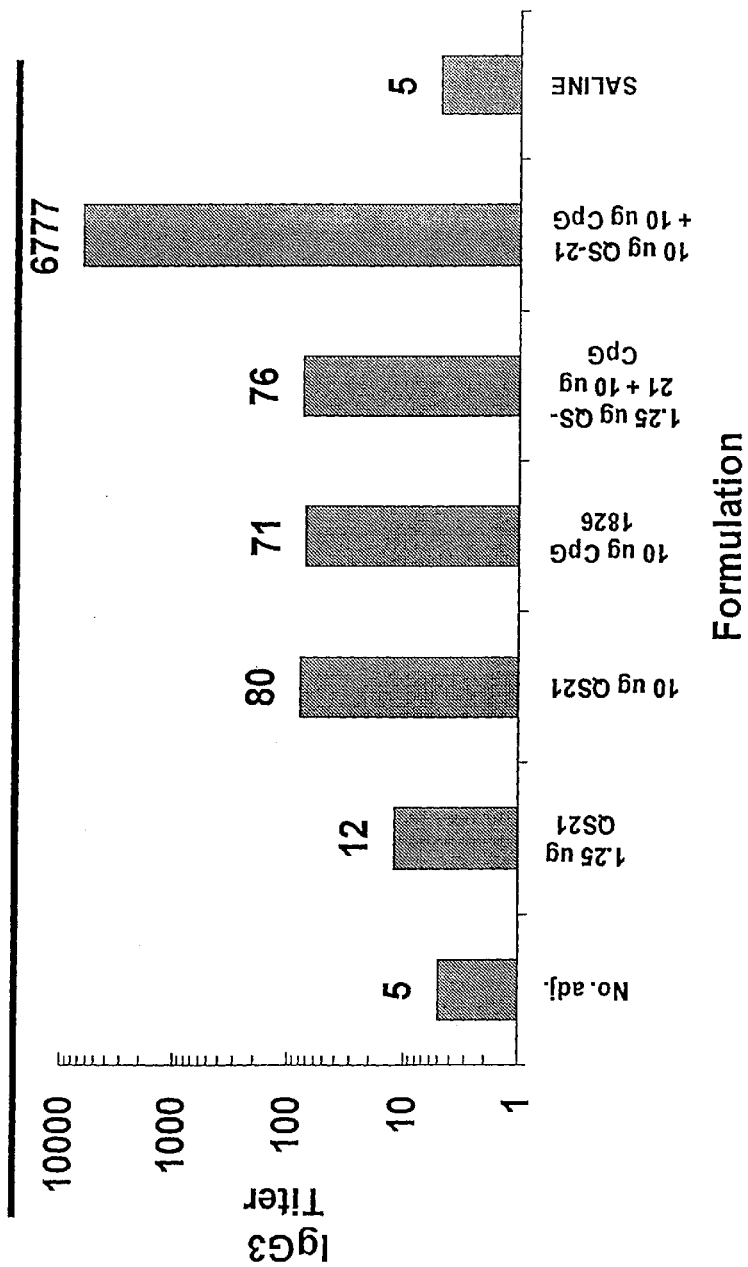
FIG. 6 provides a bar graph of IgG3 titers specific for pneumococcal Type 14 polysaccharide with the various formulations and/or combinations of QS-21 and CpG oligonucleotide in mouse sera collected 21 days after a first immunization given on day 0.

Sera from mice receiving a single immunization was collected at day 21. Sera from mice receiving 2 immunizations was collected at day 42. Antibody titers specific for Type 14 polysaccharide was determined on the sera. IgG subclasses IgG1, IgG2a, and IgG3 were determined for an equivolume sera pool from the mice in each group. After a single immunization, IgG1 titers were 66 fold higher for the 10 μg QS-21/10 μg CpG combination than for QS-21 alone and were 43 fold higher than for CpG alone (FIG. 4). IgG2a titers were 11 fold higher for the 10 μg QS-21/CpG combination than for either QS-21 alone or CpG alone (FIG. 5). IgG3 titers were 85 fold higher for the 10 μg QS-21/CpG combination than for QS-21 alone and were 95 fold higher than for CpG alone (FIG. 6).

Figure 7:
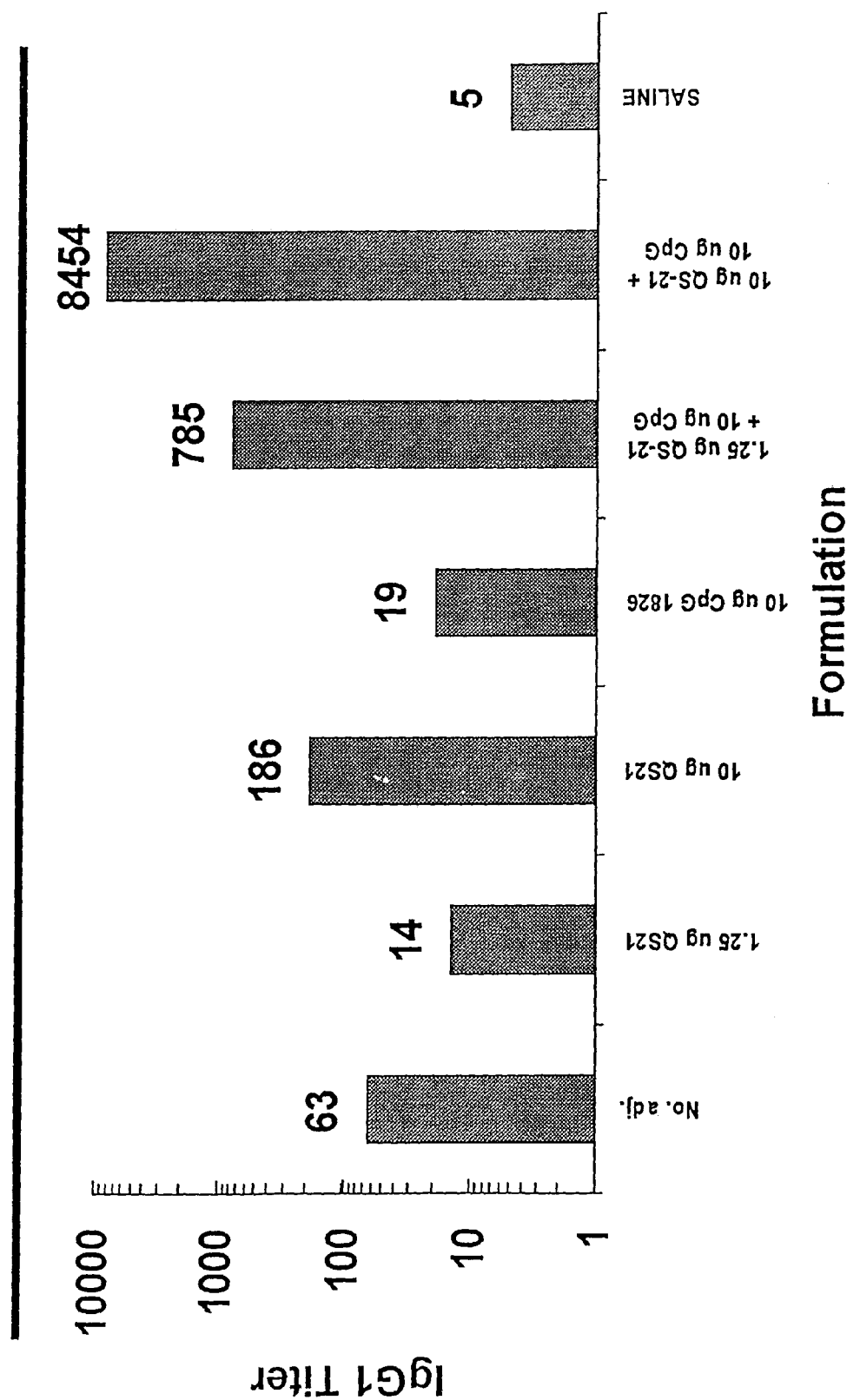
FIG. 7 depicts a bar graph of IgG1 titers specific for pneumococcal Type 14 polysaccharide with the various formulations and/or combinations of QS-21 and CpG oligonucleotide in mouse sera collected 14 days after a second immunization given 28 days after the first immunization.
Figure 8:
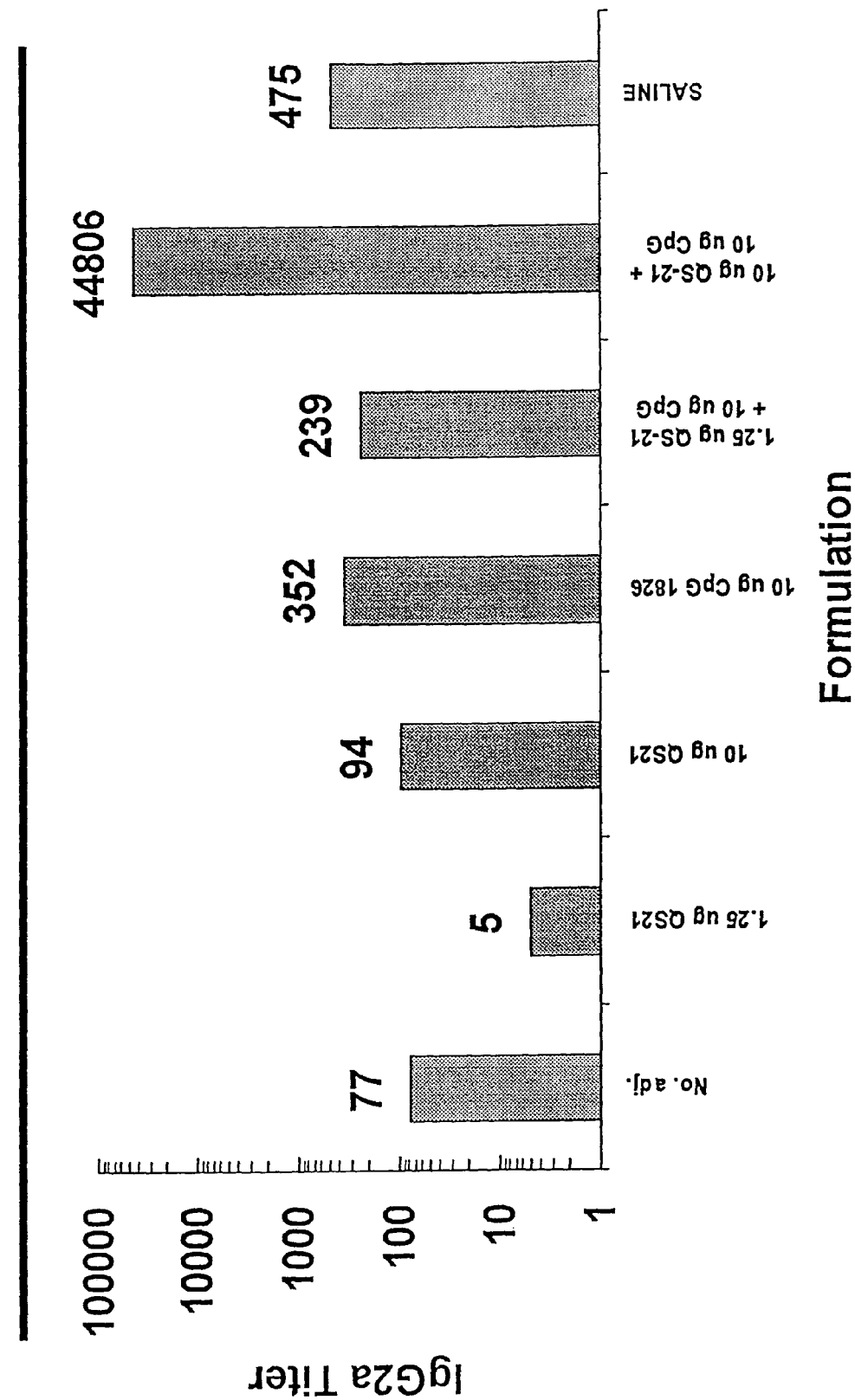
FIG. 8 provides a bar graph of IgG2a titers specific for pneumococcal Type 14 polysaccharide with the various formulations and/or combinations of QS-21 and CpG oligonucleotide in mouse sera collected 14 days after a second immunization given 28 days after the first immunization.
Figure 9:
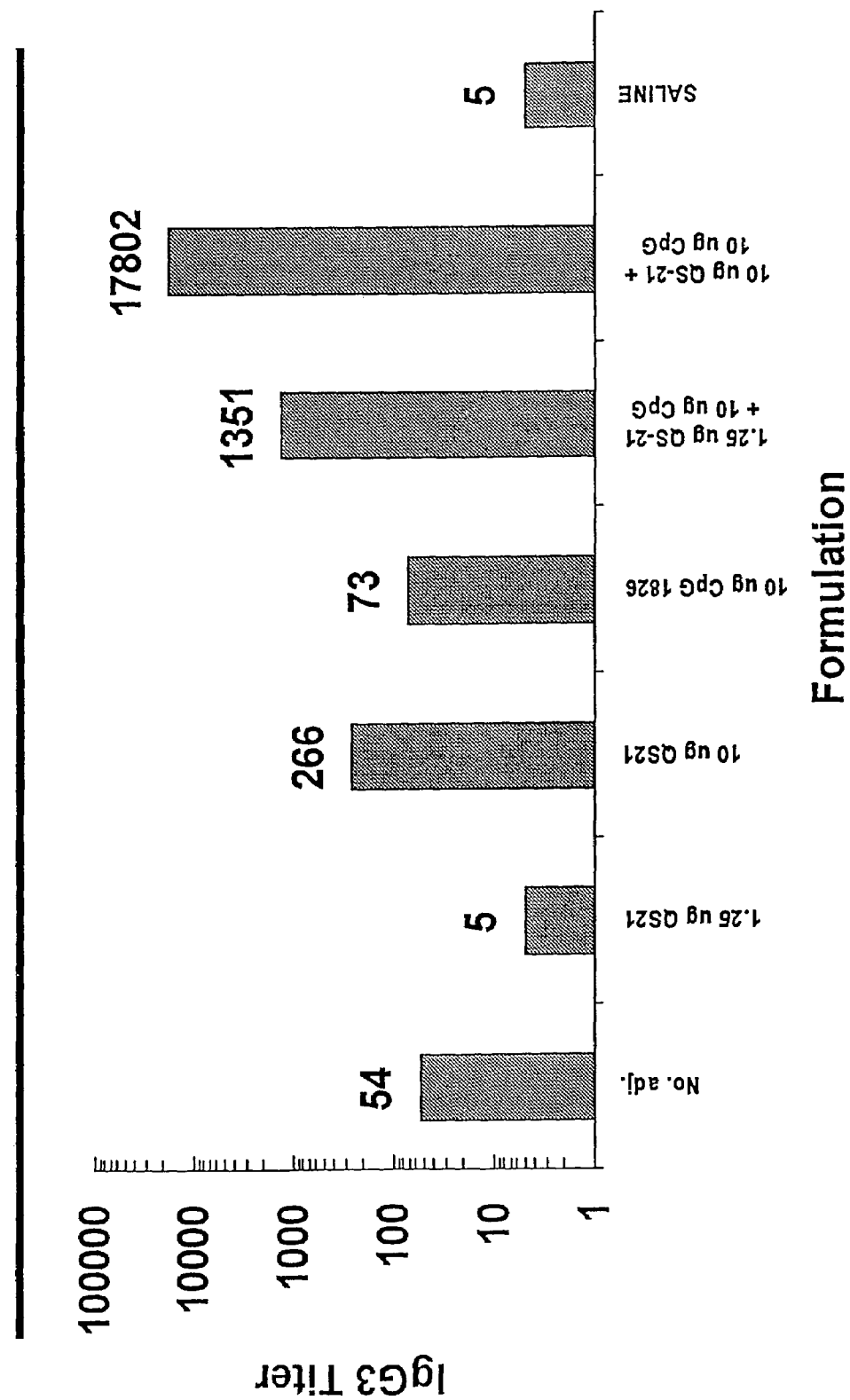
FIG. 9 shows a bar graph of IgG3 titers specific for pneumococcal Type 14 polysaccharide with the various formulations and/or combinations of QS-21 and CpG oligonucleotide in mouse sera collected 14 days after a second immunization given 28 days after the first immunization.

After two immunizations, IgG1 titers were 46 fold higher for the 10 μg QS-21/CpG combination than for QS-21 alone and were 444 fold higher than for CpG alone (FIG. 7). IgG2a titers were 476 fold higher for the 10 μg QS-21/CpG combination than for QS-21 alone and were 127 fold higher than for CpG alone (FIG. 5). IgG3 titers were 67 fold higher for the 10 μg QS-21/CpG combination than for QS-21 alone and were 243 fold higher than for CpG alone (FIG. 9). The enhancement of these titers shows that this is a positive synergistic effect and is not simply an additive adjuvant effect of combining these two adjuvants. In addition, the combination of low doses of QS-21 (1.25 μg) with 10 μg CpG also produced IgG1 and IgG3 titers after two immunizations that were higher than those produced by either 1.25 μg QS-21 alone, 10 μg QS-21 alone, or 10 μg CpG alone.

The invention now being fully described, it will be apparent to one of ordinary skill in the art that many changes and modifications can be made thereto without departing from the spirit or scope of the invention as set forth below.

wherein the immunostimulatory oligonucleotide is not a part of a DNA vaccine vector, and wherein the saponin and immunostimulatory oligonucleotide have a synergistic adjuvant effect.

2. The immune adjuvant composition as claimed in claim 1, wherein the saponin comprises a substantially pure saponin.

3. The immune adjuvant composition as claimed in claim 2, wherein the substantially pure saponin is QS-7, QS-17, QS-18, or QS-21.

4. The immune adjuvant composition as claimed in claim 3, wherein the substantially pure saponin is QS-21.

5. The immune adjuvant composition as claimed in claim 1 or 4, wherein the immunostimulatory oligonucleotide comprises more than one unmethylated CpG dinucleotide.

6. The immune adjuvant composition as claimed in claim 1 or 4, wherein the immunostimulatory oligonucleotide comprises at least one chemical group selected from the group consisting of phosphorothioate, alkylphosphonate, phophorodithioate, alkylphosphorothioate, phosphoramidate, 2-O-methyl, carbamate, acetamidate, carboxymethyl ester, carbonate, and phosphate triester.

7. The immune adjuvant composition as claimed in claim 1 or 4, wherein the immunostimulatory oligonucleotide comprises at least one phosphorothioate modified nucleotide.

8. The immune adjuvant composition as claimed in claim 1, wherein the immunostimulatory oligonucleotide comprises a CpG motif having the formula 5'$X_1$CG$X_2$3', wherein $X_1$ is adenine, guanine, or thymine, and $X_2$ is cytosine, thymine, or adenine.

9. The immune adjuvant composition as claimed in claim 1 or 4, wherein the immunostimulatory oligonucleotide comprises TCTCCCAGCGTGCGCCAT (SEQ ID NO:1).

10. An immune adjuvant composition comprising

I claim:

1. An immune adjuvant composition comprising (a) a saponin possessing immune adjuvant activity, wherein the saponin is derived from *Quillaja saponaria*; and (b) an immunostimulatory oligonucleotide comprising at least one unmethylated CpG dinucleotide, (a) a saponin possessing immune adjuvant activity, wherein the saponin is derived from *Quillaja saponaria*; and (b) an immunostimulatory oligonucleotide comprising at least one unmethylated CpG dinucleotide, wherein the saponin is substantially pure, and the saponin is QS-7, QS-17 or QS-18, and wherein the saponin and immunostimulatory oligonucleotide have a synergistic adjuvant effect.

11. A method for inducing an immune response in an individual to an antigen comprising (1) administering an amount of the immune adjuvant composition as claimed in claim 10 to the individual; and (2) administering a nucleic acid molecule comprising a nucleotide sequence encoding the antigen to the individual, wherein (1) and (2) induce an immune response in the individual to the antigen.

12. An immune adjuvant composition comprising
(a) a saponin possessing immune adjuvant activity, wherein the saponin is derived from *Quillaja saponaria*; and
(b) an immunostimulatory oligonucleotide comprising at least one unmethylated CpG dinucleotide,
wherein the immunostimulatory oligonucleotide comprises at least one chemical group selected from the group consisting of phosphorothioate, alkylphosphonate, phophorodithioate, alkylphosphorothioate, phosphoramidate, 2-O-methyl, carbamate, acetamidate, carboxymethyl ester, carbonate, and phosphate triester, and
wherein the saponin and immunostimulatory oligonucleotide have a synergistic adjuvant effect.

13. The immune adjuvant composition as claimed in claim 12, wherein the immunostimulatory oligonucleotide comprises at least one phosphorothioate modified nucleotide.

14. A method for inducing an immune response in an individual to an antigen comprising (1) administering an amount of the immune adjuvant composition as claimed in claim 12 to the individual; and (2) administering a nucleic acid molecule comprising a nucleotide sequence encoding the antigen to the individual, wherein (1) and (2) induce an immune response in the individual to the antigen.

15. A method for inducing an immune response in an individual to an antigen comprising (1) administering an amount of the immune adjuvant composition as claimed in claim 13 to the individual; and (2) administering a nucleic acid molecule comprising a nucleotide sequence encoding the antigen to the individual, wherein (1) and (2) induce an immune response in the individual to the antigen.

16. An immune adjuvant composition comprising
(a) a saponin possessing immune adjuvant activity, wherein the saponin is derived from *Quillaja saponaria*; and
(b) an immunostimulatory oligonucleotide comprising at least one unmethylated CpG dinucleotide,
wherein the immunostimulatory oligonucleotide comprises TCTCCCAGCGTFCGCCAT (SEQ ID NO:1), and,
wherein the saponin and immunostimulatory oligonucleotide have a synergistic adjuvant effect.

17. A method for inducing an immune response in an individual to an antigen comprising (1) administering an amount of the immune adjuvant composition as claimed in claim 16 to the individual; and (2) administering a nucleic acid molecule comprising a nucleotide sequence encoding the antigen to the individual, wherein (1) and (2) induce an immune response in the individual to the antigen.

18. An immune adjuvant composition comprising
(a) a saponin possessing immune adjuvant activity, wherein the saponin is derived from *Quillaja saponaria*; and
(b) an immunostimulatory oligonucleotide comprising at least one unmethylated CpG dinucleotide,
wherein the immunostimulatory oligonucleotide comprises TCCATGACGTTCCTGACGTT (SEQ ID NO:2), and
wherein the saponin and immunostimulatory oligonucleotide have a synergistic adjuvant effect.

19. A method for inducing an immune response in an individual to an antigen comprising (1) administering an amount of the immune adjuvant composition as claimed in claim 18 to the individual; and (2) administering a nucleic acid molecule comprising a nucleotide sequence encoding the antigen to the individual, wherein (1) and (2) induce an immune response in the individual to the antigen.

20. An immune adjuvant composition comprising
(a) a saponin possessing immune adjuvant activity, wherein the saponin is derived from *Quillaja saponaria*; and
(b) an immunostimulatory oligonucleotide comprising at least one unmethylated CpG dinucleotide, wherein the immunostimulatory oligonucleotide is 4–40 bases in length, and
wherein the saponin and immunostimulatory oligonucleotide have a synergistic adjuvant effect.

21. A method for inducing an immune response in an individual to an antigen comprising (1) administering an amount of the immune adjuvant composition as claimed in claim 20 to the individual; and (2) administering a nucleic acid molecule comprising a nucleotide sequence encoding the antigen to the individual, wherein (1) and (2) induce an immune response in the individual to the antigen.

22. An immune adjuvant composition comprising
(a) a saponin possessing immune adjuvant activity, wherein the saponin (i) is derived from *Quillaja saponaria* and (ii) is a chemically modified saponin; and
(b) an immunostimulatory oligonucleotide comprising at least one unmethylated CpG dinucleotide,
wherein the saponin and immunostimulatory oligonucleotide have a synergistic adjuvant effect.

23. A method for inducing an immune response in an individual to an antigen comprising (1) administering an amount of the immune adjuvant composition as claimed in claim 22 to the individual; and (2) administering a nucleic acid molecule comprising a nucleotide sequence encoding the antigen to the individual, wherein (1) and (2) induce an immune response in the individual to the antigen.

24. The composition of claim 1, wherein the saponin is a chemically modified saponin.

25. The immune adjuvant composition as claimed in claim 1 or 4, wherein the immunostimulatory oligonucleotide comprises TCCATGACGTTCCTGACGTT (SEQ ID NO:2).

26. A method for inducing an immune response in an individual to an antigen comprising (1) administering an amount of the immune adjuvant composition as claimed in claim 1 to the individual; and (2) administering a nucleic acid molecule comprising a nucleotide sequence encoding the antigen to the individual, wherein (1) and (2) induce an immune response in the individual to the antigen.

27. The method as claimed in any of claims 14, 15, 17, 19, 21, 23, or 26, wherein the saponin comprises is a substantially pure saponin.

28. The method as claimed in claim 27, wherein the substantially pure saponin is QS-7, QS-17, QS-18, or QS-21.

29. The method as claimed in claim 28, wherein the substantially pure saponin is QS-21.

30. The method as claimed in any of claims 11, 14, 15, 17, 19, 21, 23, or 26, wherein the immunostimulatory oligonucleotide comprises more than one unmethylated CpG dinucleotide.

31. The method as claimed in any of claims 11, 17, 19, 21, 23, or 26, wherein the immunostimulatory oligonucleotide comprises at least one chemical group selected from the group consisting of phosphorothioate, alkylphosphonate, phophorodithioate, alkylphosphorothioate, phosphoramidate, 2-O-methyl, carbamate, acetamidate, carboxymethyl ester, carbonate, and phosphate triester.

32. The method as claimed in any of claims 11, 17, 19, 21, 23, or 26, wherein the immunostimulatory oligonucleotide comprises at least one phosphorothioate modified nucleotide.

33. The method as claimed in any of claims 11, 14, 15, 17, 19, 21, 23, or 26, wherein the immunostimulatory oligonucleotide comprises a CpG motif having the formula $5'X_1CGX_23'$, wherein $X_1$ is adenine, guanine, or thymine, and $X_2$ is cytosine, thymine, or adenine.

34. The method as claimed in any of claims 11, 14, 15, 21, 23, or 26, wherein the immunostimulatory oligonucleotide comprises TCTCCCAGCGTGCGCCAT (SEQ ID NO:1) or TCCATGACGTTCCTGACGTT (SEQ ID NO:2).

35. The method as claimed in any of claims 11, 14, 15, 21, 19, 21, 23, or 26, wherein the individual is an animal.

36. The method as claimed in claim 35, wherein the animal is a mammal.

37. The method as claimed in any of claims 11, 14, 15, 21, 19, 21, 23, or 26, wherein the individual is a human.

38. A vaccine composition comprising
   (a) a saponin possessing immune adjuvant activity, wherein the saponin is derived from *Quillaja saponaria*;
   (b) an immunostimulatory oligonucleotide comprising at least one unmethylated CpG dinucleotide; and
   (c) a nucleic acid molecule comprising a nucleotide sequence encoding an antigen, wherein the nucleotide sequence is operatively linked to a promoter,
   wherein the immunostimulatory oligonucleotide is not a part of the nucleic acid molecule comprising the nucleotide sequence encoding the antigen.

39. The vaccine composition as claimed in claim 38, wherein the saponin is a substantially pure saponin.

40. The vaccine composition as claimed in claim 39, wherein the substantially pure saponin is QS-7, QS-17, QS-18, or QS-21.

41. The vaccine composition as claimed in claim 40, wherein the substantially pure saponin is QS-21.

42. The vaccine composition as claimed in claim 38, wherein the immunostimulatory oligonucleotide comprises more than one unmethylated CpG dinucleotide.

43. The vaccine composition as claimed in claim 38, wherein the immunostimulatory oligonucleotide comprises at least one chemical group selected from the group consisting of phosphorothioate, alkylphosphonate, phophorodithioate, alkylphosphorothioate, phosphoramidate, 2-O-methyl, carbamate, acetamidate, carboxymethyl ester, carbonate, and phosphate triester.

44. The vaccine composition as claimed in claim 38, wherein the immunostimulatory oligonucleotide comprises at least one phosphorothioate modified nucleotide.

45. The vaccine composition as claimed in claim 38, wherein the immunostimulatory oligonucleotide comprises a CpG motif having the formula $5'X_1CGX_23'$, wherein $X_1$ is adenine, guanine, or thymine, and $X_2$ is cytosine, thymine, or adenine.

46. The vaccine composition as claimed in claim 38 or 41, wherein the immunostimulatory oligonucleotide comprises TCTCCCAGCGTGCGCCAT (SEQ ID NO:1) or TCCATGACGTTCCTGACGTT (SEQ ID NO:2).

47. The method of any of claims 11, 17, 19, 23, or 26, wherein the nucleic acid molecule encoding the antigen is administered to the individual concurrently with the immune adjuvant composition.

48. The method of any of claims 14, 15, or 21, wherein the nucleic acid molecule encoding the antigen is administered to the individual concurrently with the immune adjuvant composition.

49. The method as claimed in any of claims 14, 15, 21, 23, and 26, wherein the saponin is substantially pure, wherein the saponin is QS-21, and wherein the immunostimulatory oligonucleotide comprises TCTCCCAGCGTGCGCCAT (SEQ ID NO:1 or TCCATGACGTTCCTGACGTT (SEQ ID NO:2).

50. The immune adjuvant composition as claimed in claim 12 or 20, wherein the saponin is chemically modified.

51. The immune adjuvant composition as claimed in claim 12, 20 or 22, wherein the immunostimulatory oligonucleotide comprises TCTCCCAGCGTGCGCCAT (SEQ ID NO:1) or TCCATGACGTTCCTGACGTT (SEQ ID NO:2).

52. The immune adjuvant composition as claimed in claim 12 or 22, wherein the saponin is substantially pure.

53. The immune adjuvant composition as claimed in claim 52, wherein the saponin is QS-21.

54. The immune adjuvant composition as claimed in claim 53, wherein the immunostimulatory oligonucleotide comprises TCTCCCAGCGTGCGCCAT (SEQ ID NO:1) or TCCATGACGTTCCTGACGTT (SEQ ID NO:2).

55. The immune adjuvant composition as claimed in claim 20, wherein the saponin is substantially pure.

56. The immune adjuvant composition as claimed in claim 55, wherein the saponin is QS-21.

57. The immune adjuvant composition as claimed in claim 20 or 56, wherein the immunostimulatory oligonucleotide comprises at least one chemical group selected from the group consisting of phosphorothioate, alkylphosphonate, phophorodithioate, alkylphosphorothioate, phosphoramidate, 2-O-methyl, carbamate, acetamidate, carboxymethyl ester, carbonate, and phosphate triester.

58. The immune adjuvant composition as claimed in claim 56, wherein the immunostimulatory oligonucleotide comprises TCTCCCAGCGTGCGCCAT (SEQ ID NO:1) or TCCATGACGTTCCTGACGTT (SEQ ID NO:2).

59. The immune adjuvant composition as claimed in claim 16 or 18, wherein the saponin is substantially pure.

60. The immune adjuvant composition as claimed in claim 59, wherein the saponin is QS-21.

* * * * *

SEQUENCE LISTING

<160> NUMBER OF SEQ ID NOS: 2

<210> SEQ ID NO 1
<211> LENGTH: 18
<212> TYPE: DNA
<213> ORGANISM: Quillaja saponaria

<400> SEQUENCE: 1
tctcccagcg tgcgccat                                                18

<210> SEQ ID NO 2
<211> LENGTH: 20
<212> TYPE: DNA
<213> ORGANISM: Quillaja saponaria

<400> SEQUENCE: 2
tccatgacgt tcctgacgtt                                              20